United States Patent [19]

Kim et al.

[11] 4,180,556
[45] Dec. 25, 1979

[54] PRETREATMENT METHOD FOR CARCINOEMBRYONIC ANTIGEN ASSAY

[75] Inventors: Yung D. Kim, Lindenhurst; Joseph T. Tomita; Jay R. Schenck, both of Waukegan, all of Ill.

[73] Assignee: Abbott Laboratories, North Chicago, Ill.

[21] Appl. No.: 916,381

[22] Filed: Jun. 16, 1978

Related U.S. Application Data

[63] Continuation-in-part of Ser. No. 776,019, Mar. 9, 1977, abandoned.

[51] Int. Cl.$^2$ .................... G01N 33/16; A61K 39/00
[52] U.S. Cl. ........................................ 424/1; 424/12; 23/230 B
[58] Field of Search .................... 424/1, 12; 23/230 B; 240/112 R, 112 B

[56] References Cited

U.S. PATENT DOCUMENTS

| 3,663,684 | 5/1972 | Freedman et al. | 424/1 |
| 3,867,363 | 2/1975 | Hansen | 424/1 |

OTHER PUBLICATIONS

Kolthoff et al., *Textbook of Quantitative Inorganic Analyses*, 3rd Ed. MacMillan Co., N.Y. (1952), pp. 398–400.
Ashman et al., Clinica Animia Acta, vol. 74 (1977), pp. 77–84.
Tatarinov et al., Chem. Abstracts, vol. 82, No. 19 (1975), Abstract #123040p.
Duraiswami et al., Chem. Abstracts, vol. 84, No. 25, (1976), Abstract #178102g.

*Primary Examiner*—Richard E. Schafer
*Assistant Examiner*—Christine M. Nucker
*Attorney, Agent, or Firm*—Neal O. Willmann

[57] ABSTRACT

An improvement in a method for the separation of carcinoembryonic antigen (CEA) from a plasma sample preparatory to conducting an assay for said antigen is disclosed.

8 Claims, No Drawings

PRETREATMENT METHOD FOR CARCINOEMBRYONIC ANTIGEN ASSAY

CROSS-REFERENCE TO RELATED APPLICATION

This application is a continuation-in-part of our earlier application Ser. No. 776,019, filed Mar. 9, 1977, now abandoned.

BACKGROUND OF THE INVENTION

Since the discovery of a tumor-associated antigen, various methods for measuring the level of carcinoembryonic antigen (CEA) in sera or plasma have been described. Several of these methods employ radioimmunoassay (RIA) procedures. Generally, two different assay approaches have been suggested. In one approach, the specimen, e.g., plasma, is pretreated to separate the carcinoembryonic antigen material from other materials present in the specimen. In such an approach, a glycoprotein solvent, such as perchloric acid, is employed followed by time consuming dialysis to separate the soluble CEA-containing material from the other material present in the specimen. In the second general approach, no pretreatment of the specimen with such a solvent is employed. Instead, the specimen (e.g., plasma) is subjected to a so-called double-antibody treatment. This latter method has the disadvantage of requiring highly specific antibodies that are not readily available and also a relatively long period of time (two or three days) to perform the assay.

SUMMARY OF THE INVENTION

Briefly, Applicants have developed an improved method for measuring the level of carcinoembryonic antigen (CEA) in a specimen by pretreating with perchloric acid to dissociate the CEA material from binding proteins, separating said precipitate from the CEA-containing supernatant and measuring the level of CEA, wherein the improvement comprises eliminating the necessity of dialysis to purify the perchloric acid treated specimen by:

(a) adding to said CEA-containing supernatant a buffered source of potassium ions to precipitate potassium perchlorate; and (b) separating said potassium perchlorate precipitate to yield a CEA-containing supernatant ready for assay.

DESCRIPTION OF THE PREFERRED EMBODIMENTS

In the improved method, a specimen of blood to be assayed is obtained. If the specimen is in the form of whole blood, it is preferably first treated to obtain a plasma specimen. As is well known in the art, a plasma specimen can be obtained by mixing an anticoagulant, such as ethylenediaminetraacetate, with the whole blood specimen and subjecting the resulting mixture to centrifugation to separate erythrocytes, yielding a plasma specimen as the supernatant. If desired, the plasma sample can be stored at low temperature, e.g., about 4° C. for up to about 12 hours, or frozen, until the time of pretreatment hereinafter described.

For convenience, a dilute salt solution of the plasma is prepared to provide sufficient quantities for the performance of the assay. Generally, about 20 to 50% v/v plasma and about 50 to 80% dilute salt solution are mixed with a vortex mixer. A particularly preferred solution comprises 40% plasma and 60% saline solution. During the mixing, perchloric acid, a glycoprotein solvent, is added to precipitate binding and non-specific plasma proteins and thereby dissociate complexes of CEA and binding proteins. Centrifugation results in the separation of any CEA material present in the plasma specimen from the precipitated binding and non-specific plasma proteins.

After separation of the insoluble proteins, the supernatant comprises glycoproteins, perchlorate ions and CEA material. To this supernatant is added an aqueous, buffered source of potassium ions. This will result in the removal of perchlorate ions from the supernatant by the formation of insoluble $KClO_4$. The buffer is necessary to elevate the pH of the supernatant and insure the insolubility of the $KClO_4$. It is also preferred, but not required, that the temperature of the buffered source of potassium ions be about 4° C. to about 10° C., so that the temperature of the reaction medium is maintained at or about 25° C.

The removal of perchlorate ions by precipitation with potassium ions can be achieved by adding any aqueous source of buffered potassium. For example, Applicants have employed KOH, KCl, potassium acetate, and potassium biphthalate. The potassium ions are ideally provided in a buffer to elevate the pH of the perchloric acid solution and to preserve the potassium perchlorate precipitate. Suitable buffers include $K_2HPO_4$, potassium acetate, NaOH, $Na_2HPO_4.7H_2O$ and potassium biphthalate.

The insoluble saltes formed during the addition of the buffered potassium ions are separated from the neutralized CEA-containing supernatant to yield a CEA-containing supernatant ready for assay.

The separation of CEA material does not require any dialysis step and can be done using various techniques, including sedimentation and decantation. A preferred separation method is centrifugation. Generally, centrifugation in the range of about 50 xg to about 850 xg for about one minute to above five minutes has been found to produce satisfactory results.

The pretreatment method of the present invention may be further understood by reference to the following illustrative examples.

EXAMPLE 1

0.4 ml of a frozen plasma sample derived from human blood was placed in a test tube and allowed to reach ambient temperature. The sample was then diluted with 0.6 ml of 0.9% NaCl solution. While stirring with a vortex mixer, 1.0 ml of cold 1.2 M perchloric acid (PCA) solution was added and the mixing continued for 10 seconds. The temperature of the PCA at the time of addition was about 4° C. The resulting mixture, which included a precipitate, was centrifuged at about 850 xg for about 30 minutes at about 4° C. After the centrifugation, 1.2 ml of of the supernatant was pipetted into a new test tube. Approximately 0.21 ml of neutralizing agent, which was a phosphate buffer at a temperature of about 4° C. and consisting of a mixture of 5 M KOH and 3 M $K_2HPO_4$ in the ratio of 8.2:5.0 (v/v) was added quickly so that the mixture yielded a final pH value of 6.5±0.2. A salt, $KClO_4$, produced in the mixture was only sparingly soluble in the phosphate and precipitated. The precipitate was subjected to centrifugation at 850 xg for 3 minutes at 4° C. The salt concentration of the supernatant was approximately 0.15 M phosphate. The supernatant was then ready for CEA assay.

EXAMPLE 2

In this example, a CEA assay employing a method of the present invention was carried out and results thereof were compared with the results of a CEA assay using the commercial method referred to in the prior art as the CEA-Roche Z-gel method.

A supernatant as prepared in Example 1, was employed in this example in a solid-phase radioimmunoassay using antibody-coated tubes. In this so-called "Sandwich" RIA, polystyrene tubes (13×100 mm) were coated with CEA antibody according to prior art techniques. Specifically, a mixture of 1.1 ml of guinea pig anti-CEA antibody and IgG prepared by diethylaminoethyl cellulose fractionation (300 ug/ml) in a buffer was used to coat the polystyrene tubes. The buffer employed in the mixture consisted of 0.01 M tris-HCl and 0.15 M NaCl having a pH of 9. The guinea pig anti-CEA antibody was obtained by prior art techniques previously described by Tomita, et al., Immunol., 26, 291 (1974), and Anderson, et al., Immunochem., 12, 577 (1975).

After coating with the above-described mixture, the tubes were incubated for about 16 hours at 37° C. and then 2 hours at 4° C. After removing the coating solution, the tubes were stored in 1.0 ml. of 0.01 M tris-saline solution containing 0.1% azide pH 7 at 4° C. and washed with the same buffer just prior to use.

Guinea pig anti-CEA antibody as described above was radiolabeled with $I^{125}$ by the insoluble lactoperoxidase method described by David, et al., Biochem., 13, 1014 (1974).

To establish a standard curve, 1.0 ml. of known standard CEA samples in 1% bovine serum albumin (BSA), 0.15 M phosphate buffer pH 6.5±0.2 were added into a series of the antibody coated tubes. For the unknown samples 1.0 ml. of the clear supernatant from Example 1, was transferred into an antibody-coated tube and then the tubes were incubated for 2 hours at 45° C. At the end of the incubation period, the samples were aspirated and the tubes washed twice with 1.5 ml. each of 0.01 M tris-saline 0.01% azide pH 7 buffer. Then 1.0 ml. of $I^{125}$ labeled antibody (approximately 50 ng., 200,000 c/m) in 1% BSA, in 0.15 M phosphate buffer solution was added to each tube and the tubes were incubated for a second time for 2 hours at 45° C. After the second incubation, the solution was removed and the tubes were washed twice with the tris-saline buffer before counting in a Packard gamma counter. The CEA levels of the unknown samples were determined from the standard curve and corrected for dilution.

The effects of incubation-times on the binding of CEA to the antibody-coated tubes was studied by incubating a series of identical CEA samples at 45° C. and stopping the reaction at appropriate time intervals by aspiration of the content of the tubes. Then, labeled antibody solution was added and the tubes were incubated overnight at 37° C.

The equilibrium binding of CEA to antibody-coated tubes at 45° C. was nearly achieved after an incubation period of about 10 hours. However, 50% of the equilibrium binding of CEA was attained after only 2 hours at 45° C. Incorporation of a 2-hour incubation step permitted the CEA assay to be performed in a single day. The results were available on the following morning, after counting overnight. In contrast, the prior art CEA-Roche Z-gel method was considerably more time consuming, requiring, for example, at least 16 hours of dialysis.

The effects of variations in pH and ionic strength were studied by adjusting the pH of the perchloric acid (PCA) extracts to 6.0, 6.5 and 7.0, respectively, maintaining the ionic strength approximately constant, and by adding NaCl to increase the ionic strength ranging from 0.15 to 0.85 at a constant pH value of 6.5. The results are summarized in Table I.

As is apparent from the results shown in Table I, the assay of Example 2, showed marked tolerance to changes in both pH and ionic strength of the assay system.

Although the present invention has been described and its utility exemplified, in part, by reference to a radioimmunoassay, the present invention also can be utilized in conjunction with other assays, such as, for example, enzyme immunoassays and fluorescent assays. In addition, although one utility of the present invention has been exemplified by a direct sandwich assaying employing antibody coated tubes, it may also be used in conjunction with other types of assays and/or with other types of solid supports, such as paper discs or plastic beads.

TABLE I
EFFECTS OF pH AND SALT CONCENTRATION

| pH | Salt Concentration (M) | CEA ACTIVITY IN PLASMA SAMPLES (ng./ml.) | | |
|---|---|---|---|---|
| | | A | B | C |
| 6.0 | 0.15 | 3.4 ± 0.1 | 7.5 ± 0.0 | 3.6 ± 0.1 |
| 6.5 | 0.15 | 3.1 ± 0.1 | 6.9 ± 0.5 | 3.9 ± 0.1 |
| 6.5 | 0.50 | 3.1 ± 0.1 | 7.4 ± 0.1 | 3.3 ± 0.2 |
| 6.5 | 0.85 | 3.4 ± 0.2 | 7.6 ± 0.1 | 3.5 ± 0.0 |
| 7.0 | 0.15 | 3.5 ± 0.1 | 7.5 ± 0.1 | 3.5 ± 0.1 |

[1]Samples A, B and C were prepared by pooling two or three plasma which had been collected from patients, diagnosed as cancerous or carrying other pathological diseases.

[2]pH values were read on Radiometer pH meter model TT1C with ± 0.1 precision and adjusted by addition of an appropriate amount of neutralizing agent. Weighed NaCl crystals were added to PCA-extracts to give the desired salt concentrations, maintaining a constant pH.

[3]Each sample was assayed in duplicate, and arithmetic mean values and mean deviations are presented in the table.

While the present invention has been described by reference to certain illustrative examples, various modifications within the spirit and scope of the invention will be apparent to those skilled in the art.

What is claimed is:

1. In a method of measuring the level of carcinoembryonic antigen (CEA) in a specimen by pretreating with perchloric acid to dissociate the CEA material from binding proteins by precipitating said binding proteins, separating said precipitate from the CEA-containing supernatant, and measuring the level of CEA wherein the improvement comprises eliminating the necessity of dialysis to purify the perchloric acid treated specimen by:
   (a) adding to said CEA-containing supernatant a buffered source of potassium ions to precipitate potassium perchlorate; and
   (b) separating said potassium perchlorate precipitate to yield a CEA-containing supernatant ready for assay.

2. A method as described in claim 1 wherein the specimen is human plasma or serum.

3. A method as described in claim 1 wherein the buffered source of potassium ions yields a pH of the treated sample in the range of about 4.5 to 8.0.

4. A method as described in claim 1 wherein the buffered source of potassium ions is a mixture of KOH and $K_2HPO_4$.

5. A method as described in claim 1 wherein said CEA-containing supernatant is assayed using a solid phase radioimmunoassay.

6. A method as described in claim 1 wherein said neutralized CEA-containing supernatant is assayed using an immunoassay.

7. A relatively rapid, sensitive assay for measuring the CEA level in a specimen, said assay characterized by tolerance toward changes in system pH and ionic strength and comprising the steps of:

(a) pretreating a specimen of blood with a perchloric acid;

(b) centrifuging the mixture from step (a) to obtain a CEA-containing supernatant.

(c) adding to said supernatant a buffered source of potassium ions to precipitate potassium perchlorate;

(d) separating without dialysis, said salt to yield a CEA-containing supernatant;

(e) incubating a support having a coating of CEA antibody thereon with a known amount of said supernatant from step (d), to thereby bind any CEA present in said supernatant to said coating of antibody;

(f) washing said thus coated support;

(g) incubating said washed support with a known amount of labeled CEA antibody to produce a layer of labeled antibody bound to the CEA on the antibody coated support;

(h) washing the labeled, coated support of step (g); and (i) detecting quantitatively the amount of labeled antibody on the washed, labeled and coated support to thereby obtain information directly related to the level of CEA present in the specimen.

8. A relatively rapid, sensitive assay for measuring the CEA level in a specimen, said assay characterized by tolerance toward changes in system pH and ionic strength and comprising the steps of:

(a) pretreating a specimen of blood with a perchloric acid;

(b) centrifuging the mixture from step (a) to obtain a CEA-containing supernatant;

(c) adding to said supernatant a buffered source of potassium ions to precipitate potassium perchlorate;

(d) separating without dialysis, said salt to yield a CEA-containing supernatant;

(e) incubating a support having a coating of CEA antibody thereon with a known amount of said supernatant from step (d) and with a known amount of labeled CEA to thereby permit competition between the labeled CEA and any CEA present in said supernatant for antibody on the support;

(f) washing the labeled, coated support of step (e); and (g) detecting quantitatively the amount of labeled CEA on the washed, labeled and coated support to thereby obtain information directly related to the level of CEA present in the specimen.

* * * * *